(12) United States Patent
Kim (10) Patent No.: US 9,637,323 B2
(45) Date of Patent: May 2, 2017

(54) MEDICINE PACKAGE INSPECTION APPARATUS

(71) Applicant: JVM CO., LTD., Daegu (KR)

(72) Inventor: Jun Ho Kim, Daegu (KR)

(73) Assignee: JVM Co., Ltd., Daegu (KR)

( * ) Notice: Subject to any disclaimer, the term of this patent is extended or adjusted under 35 U.S.C. 154(b) by 288 days.

(21) Appl. No.: 14/483,015

(22) Filed: Sep. 10, 2014

(65) Prior Publication Data

US 2015/0070485 A1    Mar. 12, 2015

(30) Foreign Application Priority Data

Sep. 11, 2013   (KR) .................. 10-2013-0109017
Aug. 14, 2014   (KR) .................. 10-2014-0105753

(51) Int. Cl.
  *G06F 7/00*     (2006.01)
  *B65G 47/26*    (2006.01)
  *H04N 5/225*    (2006.01)
  *B65G 15/14*    (2006.01)
  *G01N 21/95*    (2006.01)

(52) U.S. Cl.
  CPC ............ *B65G 47/26* (2013.01); *B65G 15/14* (2013.01); *G01N 21/9508* (2013.01); *H04N 5/2251* (2013.01)

(58) Field of Classification Search
  None
  See application file for complete search history.

(56) References Cited

U.S. PATENT DOCUMENTS

| 6,505,461 | B1 | 1/2003 | Yasunaga |  |
|---|---|---|---|---|
| 2006/0266188 | A1 | 11/2006 | Kim |  |
| 2006/0271237 | A1 | 11/2006 | Kim |  |
| 2013/0342676 | A1* | 12/2013 | Amano | H04N 7/18 |
|  |  |  |  | 348/86 |

FOREIGN PATENT DOCUMENTS

| JP | 10162116 A | 6/1998 |
| KR | 591518 B1 | 6/2006 |
| KR | 650285 B1 | 11/2006 |

* cited by examiner

*Primary Examiner* — Yolanda Cumbess
(74) *Attorney, Agent, or Firm* — Seed IP Law Group LLP (57) ABSTRACT

Disclosed herein is a medicine package inspection apparatus for inspecting whether or not accurate medicines have been packaged in medicine packages. The medicine package inspection apparatus includes: a conveying unit conveying the medicine packages; an image reading unit photographing the medicine packages and reading states of the medicines by the photographed image; an aligning unit uniformly spreading the medicines packaged in the medicine packages unit so as not to be overlapped with each other; and a displaying means pivotably installed on a front surface of the body and displaying a work state simultaneously with controlling a work of inspecting the medicine packages. The displaying means is pivotably and tiltably installed on the body through a pivoting and tilting unit and configures a portion of the body, such that an inner portion of the body is opened when the displaying means pivots.

15 Claims, 5 Drawing Sheets

MEDICINE PACKAGE INSPECTION APPARATUS

CROSS-REFERENCE TO RELATED APPLICATIONS

This application claims priority from and the benefit of Korean Patent Application No. 10-2013-0109017, filed on Sep. 11, 2013, and Korean Patent Application No. 10-2014-0105753, filed on Aug. 14, 2014, each of which is hereby incorporated by reference for all purposes as if fully set forth herein.

BACKGROUND

Technical Field

The present disclosure relates to a medicine package inspection apparatus for inspecting whether or not accurate medicines have been packaged in medicine packages in a process of automatically packaging various medicines.

Description of the Related Art

According to the related art, a medicine automatic packaging machine receiving medicines from a plurality of cassette apparatuses in which each kind of medicines such as tablets, capsules, or the like, is accommodated and continuously packaging each dose of the medicines has been developed and used.

As the medicine automatic packaging machine according to the related art, a medicine automatic packaging machine including a plurality of cassette apparatuses disposed at an upper portion of a body and accommodating medicines such as tablets, capsules, or the like, having various sizes and shapes therein, a hopper disposed at a lower portion of the body and collecting the medicines discharged and dropping from the cassette apparatuses, a printing apparatus printing various information on a surface of packaging paper packaging the medicine, and a packaging apparatus packaging the medicines collected by the hopper using the packaging paper has been used.

It is required to inspect whether an accurate medicine has been packaged in each of medicine packages packaged by the medicine automatic packaging machine as described above. That is, since several ten to several hundred kinds of medicines are accommodated in the respective cassette apparatuses of the medicine automatic packaging machine and there is a risk that a medicine accident will occur in the case in which an inaccurate medicine is packaged, it should be necessarily inspected whether the accurate medicines are packaged in the medicine packages in which the medicines are packaged.

In addition, it should be necessarily inspected whether or not the medicines have been damaged due to a collision with a surface of the hopper, or the like, when the medicines are discharged and drop or whether or not medicines more than or less than a defined number of medicines have been packaged due to an error in a packaging operation.

According to the related art, as an apparatus for inspecting whether or not the medicine is normally packaged, an inspection apparatus including a camera photographing the medicine package in which the medicine is packaged and an image reading means determining whether or not the medicine is normally packaged through an image photographed by the camera has been known. These inspection apparatuses have been disclosed in the following patent references: Korean Patent No. 0591518; Korean Patent No. 0650285; and Japanese Patent Laid-Open Publication No. 10-162116.

However, Applicant believes there is a need to continuously improve the medicine package inspection apparatus so that the medicine package inspection apparatus may have a decreased volume and accurately convey a medicine package to be inspected and a user may easily control an inspection process and easily perform an inspection work.

BRIEF SUMMARY

Embodiments of the present invention provide a medicine package inspection apparatus that is capable of being easily treated by having a decreased entire size and is capable of smoothly and securely conveying medicine packages at the time of performing an inspection work by conveying the medicine packages by a pair of conveyor belts.

According to one embodiment of the present invention, there is provided a medicine package inspection apparatus of inspecting medicines packaged in medicine packages to confirm whether or not accurate medicines have been packaged, including: a conveying unit installed in a body and conveying the medicine packages to one side; an image reading unit photographing the medicine packages conveyed by the conveying unit and reading states of the medicines by the photographed image; an aligning unit uniformly spreading the medicines packaged in the medicine packages conveyed to the image reading unit so as not to be overlapped with each other; and a displaying means pivotably installed on a front surface of the body and displaying a work state simultaneously with controlling a work of inspecting the medicine packages, wherein the displaying means is pivotably and tiltably installed on the body through a pivoting and tilting unit and configures a portion of the body, such that an inner portion of the body is opened when the displaying means pivots.

The pivoting and tilting unit may include a pivoting member interposed between the body and the displaying means, a hinge means pivotably connecting one end of the pivoting member to the body, a first connection member connected to the other end of the pivoting member so as to be pivotable around an axis line in a vertical direction, and a second connection member connected to the first connection member so as to be pivotable around an axis line in a horizontal direction and fixed to the displaying means.

The conveying unit may include an upper conveyor apparatus having an upper belt and a plurality of upper rollers and a lower conveyor apparatus having a lower belt and a plurality of lower rollers, and the medicine packages may be conveyed in a state in which they are fitted between the upper belt and the lower belt.

The upper conveyor apparatus and the lower conveyor apparatus may receive driving power transferred from one driving source to thereby be driven.

The upper conveyor apparatus and the lower conveyor apparatus may include tension adjusting means for adjusting tension degrees of the upper belt and the lower belt, respectively.

When it is read that the medicine package inspected by the image reading unit is an abnormal medicine package, the conveying unit may reverse a conveying direction of the medicine package so that the abnormal medicine package is returned to the aligning unit.

The abnormal medicine package may be a medicine package in which a plurality of medicines are at least partially overlapped with each other or a medicine package in which a plurality of medicines contact each other to thereby be recognized as if they are one medicine.

The image reading unit may include a camera photographing a medicine package to be inspected and a light source for photographing, and the photographing may be performed through a reflecting plate so that the medicine package is photographed even in a state in which the camera and the medicine package are not put on a straight line.

The aligning unit may include at least one of a vibration means vibrating the medicine package by vibrations and a pressing means applying pressure to the medicine package.

The aligning unit may include an impact means applying impact to discontinuous fused parts discontinuously formed between the medicine packages in order to partition a medicine accommodating part in one medicine package and a medicine accommodating part in another medicine package from each other.

The aligning unit may include a guide plate guiding movement of the medicine package. The impact means may be a cam member applying impact to the medicine packages that are being moved along the guide plate. The cam member may be installed on a cam axis rotated by a motor to thereby be rotated together with the cam axis.

A plurality of cam members may be installed on a common cam axis to thereby be rotated together with the common cam axis. At least one of the plurality of cam members may form an angle of 90 degrees or more with respect to the other cam member.

The aligning unit may include a protrusion piece installed on the cam axis and a sensing part sensing a position of the protrusion piece to detect a position of the cam member.

The medicine package inspection apparatus may further include a bobbin supporting unit installed outside the body so as to support a medicine package bundle wound around a bobbin for an inspection, wherein the bobbin supporting unit includes a bobbin mounting axis into which the bobbin is detachably fitted.

The medicine package inspection apparatus may further include a cover member closing the front surface of the body together with the displaying means and moved separately from the displaying means to open an upper end portion of the front surface of the body.

DETAILED DESCRIPTION

Hereinafter, a medicine package inspection apparatus according to embodiments of the present invention will be described in detail with reference to the accompanying drawings.

Figure 1:
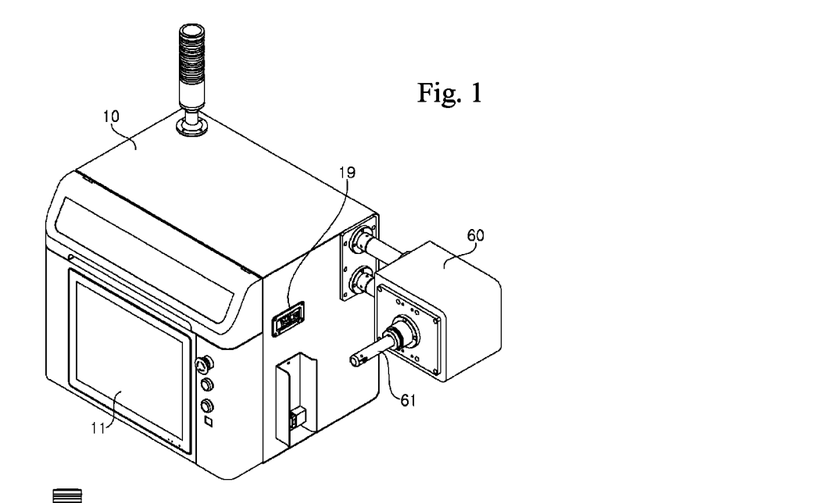
FIG. 1 is a perspective view showing a medicine package inspection apparatus according to a first example embodiment of the present invention.
Figure 2:
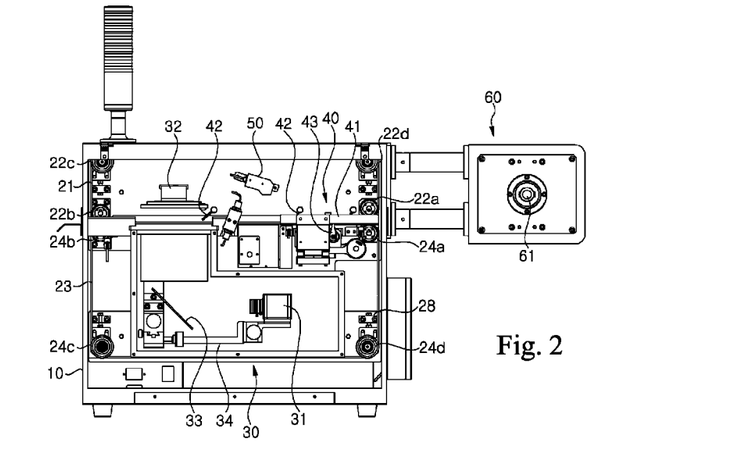
FIG. 2 is a front cross-sectional view showing the medicine package inspection apparatus according to the first example embodiment of the present invention.

As shown in FIGS. 1 and 2, a medicine package inspection apparatus according to a first example embodiment of the present invention includes a conveying unit 20 installed in a body 10 and conveying a medicine package bundle in which a plurality of medicine packages are continuously connected to each other to one side (from the right to the left when viewed in FIG. 2), an image reading unit 30 photographing the medicine packages conveyed by the conveying unit 20 and reading the number and states of the medicines by the photographed image, and an aligning unit 40 uniformly spreading the medicines packaged in the medicine packages of the medicine package bundle conveyed to the image reading unit 30 so as not to be overlapped with each other.

In addition, the medicine package inspection apparatus according to the first example embodiment of the present invention further includes a recognizing unit 50 that may recognize a mark such as a barcode, or the like, printed on a surface of the medicine package so as to detect information on the number and a kind of medicines that should be packaged in the medicine package that is being inspected and a bobbin supporting unit 60 that may support the medicine package bundle wound around a bobbin for an inspection.

As shown in FIG. 1, a displaying means 11 that may display a work state simultaneously with controlling a work of inspecting the medicine package is installed on a front surface of the body 10, and a cover member 11a that may open an inner portion of the body 10 when a user is to directly confirm the work state of the work of inspecting the medicine package with the naked eyes is installed at an upper end of the front surface of the body.

The displaying means 11 may be configured of, for example, a touch screen, or the like, and is pivotably installed on the body through a pivoting and tilting unit as described below with reference to FIGS. 4A to 4C.

The cover member 11a may close the front surface of the body 10 together with the displaying means 11 and pivot separately from an operation of the displaying means 11 to open an upper end portion of the front surface of the body 10. It is preferable that the cover member 11a is installed so as to be connected to an edge of an upper end of the body 10 through one or more hinge means to pivot upwardly.

Figure 3:
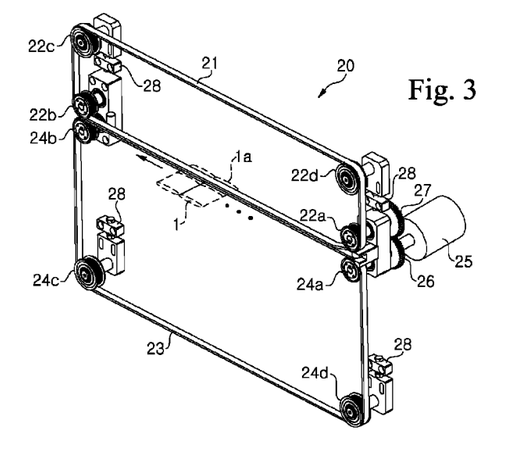
FIG. 3 is a schematic perspective view showing main components of the medicine package inspection apparatus according to the first example embodiment of the present invention for describing a conveying unit including a pair of conveyor belts for conveying a medicine package.

As shown in FIG. 3, the conveying unit 20 includes a pair of conveyor apparatus, that is, upper and lower conveyor apparatuses, arranged at upper and lower portions, respectively. The upper conveyor apparatus includes an upper belt 21 and a plurality of upper rollers 22a, 22b, 22c, and 22d disposed in the body 10 so that the upper belt 21 may be arranged in an approximately rectangular shape. In addition, the lower conveyor apparatus includes a lower belt 23 and a plurality of lower rollers 24a, 24b, 24c, and 24d disposed in the body 10 so that the lower belt 23 may be arranged in an approximately rectangular shape. According to the present invention, a medicine package 1 is conveyed in a state in which it is fitted between the upper belt 21 and the lower belt 23. To this end, the upper belt 21 and the lower belt 23 are arranged so as to contact each other over a partial section.

When the medicine package is fitted between the upper belt 21 and the lower belt 23, it is injected so that a continuous fused part 1a (See FIG. 7) continuously formed at one side of the medicine package 1 for sealing the medicine package is fitted between the upper belt 21 and the lower belt 23 in order to prevent the belts from hindering the work of inspecting the medicine packaged in the medicine package.

It is preferable that the upper and lower conveyor apparatuses are configured to receive driving power transferred from one driving source 25. The driving force of the driving source 25 may be transferred through a driving gear 26 connected to one of the upper and lower conveyor apparatuses and a driven gear 27 rotated together with the driving gear 26 depending on rotation of the driving gear 26 to thereby be connected to the other of the upper and lower conveyor apparatuses.

In FIG. 3, for example, a configuration in which the driving force of the driving source 25 is transferred to each of the upper and lower conveyor apparatuses through the driving gear 26 installed coaxially with one lower roller 24a of the lower rollers 24a, 24b, 24c, and 24d of the lower conveyor apparatus and the driven gear 27 installed coaxially with one upper roller 22a adjacent to the lower roller 24a connected to the driving gear 26 among the upper rollers 22a, 22b, 22c, and 22d of the upper conveyor apparatus is shown.

In addition, one or more upper rollers 22c and 22d of the upper rollers 22a, 22b, 22c, and 22d are provided with a tension adjusting means 28 so that the upper belt 21 may maintain appropriate tension, and one or more lower rollers 24c and 24d of the lower rollers 24a, 24b, 24c, and 24d are also provided with a tension adjusting means 28 so that the lower belt 23 may maintain appropriate tension. The tension adjusting means 28 may be configured so as to rotate, for example, a bolt to adjust a position of the upper roller or the lower roller, thereby adjusting tension of the upper belt 21 or the lower belt 23.

Referring to FIG. 2, the image reading unit 30 includes a camera 31 photographing a medicine package to be inspected and a light source, for example, a backlight 32 for photographing. In the medicine package inspection apparatus according to the present example embodiment of the present invention, since the camera 31 and the medicine package to be photographed are disposed so as not to be present on a straight line in order to decrease an entire size of the medicine package inspection apparatus, the photographing is performed through a reflecting plate 33. In order to accurately adjust a position of the camera 31 so as to be positioned at an accurate position for photographing the medicine package, a stage means 34 configured of two axes (XY) or three axes (XYZ) may be installed.

The aligning unit 40 is installed above the image reading unit 30 so that medicines in the medicine package 1 are not overlapped with each other, but may be uniformly spread before the medicine package 1 is photographed. To this end, as the aligning unit 40, at least one of a vibration means 41 vibrating the medicine package by vibrations and a pressing means applying pressure the medicine package through a brush 42, a sponge roller, or the like, may be used. The vibration means 41 may be configured to vertically or horizontally vibrate a path itself through which the medicine package is conveyed using a vibrator, a cam, or the like, generating small vibrations or be configured to apply impact to the medicine package conveyed after rotatably or vertically movable installing a vibration member 43 as shown in FIG. 2.

The aligning unit 40 according to the present example embodiment is configured to uniformly spread the medicines in the medicine package 1 using the vibration means 41 and a plurality of brushes 42.

Although the photographing by the image reading unit 30 is performed after the medicines are uniformly spread by the aligning unit 40, a state in which the medicines in the medicine package are overlapped with each other even after they pass through the aligning unit 40 may occur.

Since a medicine package in which a plurality of medicines are completely overlapped with each other, a medicine package in which a plurality of medicines are partially overlapped with each other, or a medicine package in which a plurality of medicines contact each other to thereby be recognized as if they are one medicine (hereinafter, referred to as an "abnormal medicine package") may not be normally inspected, a conveying direction of the medicine package transferred by the conveying unit 20 is reversed to again return the abnormal medicine package to the aligning unit 40.

The abnormal medicine package returned to the aligning unit 40 is reprocessed by the aligning unit 40 so that the medicines in the abnormal medicine package may be uniformly spread. As soon as the abnormal medicine package is reprocessed by the aligning unit 40, the conveying unit 20 is driven so that the reprocessed medicine package is conveyed in an initial conveying direction, that is, a forward direction.

The recognizing unit 50 is configured of, for example, a barcode scanner that may recognize a barcode. A kind and the number of medicines that are to be packaged in the medicine package 1 may be confirmed by the recognizing unit 50, and a controlling part (not shown) may receive information recognized by the recognizing unit 50 and then compare the received information with a result read by the image reading unit 30 to read whether or not an accurate kind and number of medicines have been packaged in the medicine package.

In the case in which it is read that the medicine package is the abnormal medicine package as described above as a reading result by the image reading unit 30, the conveying direction of the medicine package is reversed, such that the abnormal medicine package is conveyed in the reverse direction. The abnormal medicine package conveyed in the reverse direction and then returned again to the aligning unit 40 is reprocessed by the aligning unit 40, as described above. In this case, the conveying unit 20 is driven so that the reprocessed medicine package is again conveyed in the forward direction.

However, in the case in which a medicine having a shape different from that of medicines that are to be packaged in the medicine package is packaged in the medicine package, in the case in which the medicine is broken, in the case in which the number of medicines packaged in the medicine package is larger than that of medicines that are to be packaged in the medicine package, or the like, as a reading result by the image reading unit 30, the controlling part (not shown) may consider that a package error simply occurs and may not perform a process of returning the medicine package to the aligning unit 40 and then reprocessing the medicine package.

The bobbin supporting unit 60 is installed outside the body 10 and includes a bobbin mounting axis 61 into which a bobbin (not shown) having the medicine package bundle roundly wound therearound is detachably fitted. It is preferable the bobbin mounting axis 61 is provided with a locking means so that the bobbin mounted therein is arbitrarily separated therefrom.

The medicine package bundle supported by the bobbin supporting unit 60 is injected into the body 10 through a medicine package injection hole 19 formed in a side wall of the body 10 and is then fitted between the upper belt 21 and the lower belt 23 and conveyed, as described above.

When the medicine package wound around one bobbin is entirely unwound (that is, inspection of the medicine package bundle wound around one bobbin is completed), the user may separate the bobbin from the bobbin mounting axis 61 of the bobbin supporting unit 60 and wind another medicine package bundle to be inspected around the separated bobbin and then fit again the bobbin into the bobbin mounting axis 61 or fit another bobbin around which a medicine package bundle to be inspected is wound in advance into the bobbin mounting axis 61 and then continuously perform an inspection.

Figure 4A:
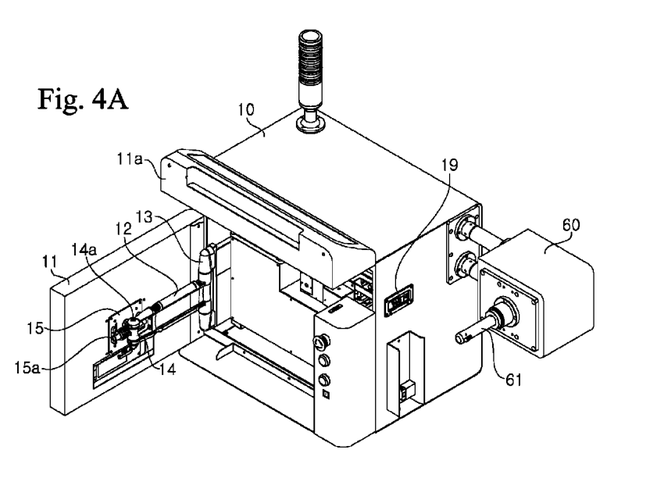
FIGS. 4A to 4C are views for describing a displaying means of the medicine package inspection apparatus according to the first example embodiment of the present invention for controlling and confirming a medicine package inspection work.
Figure 4B:
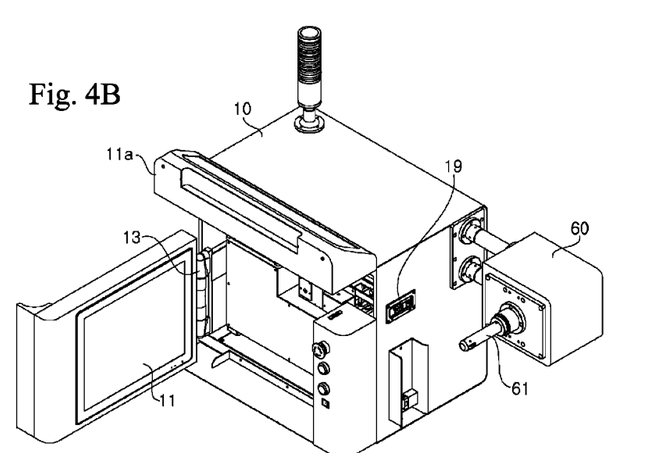
Figure 4C:
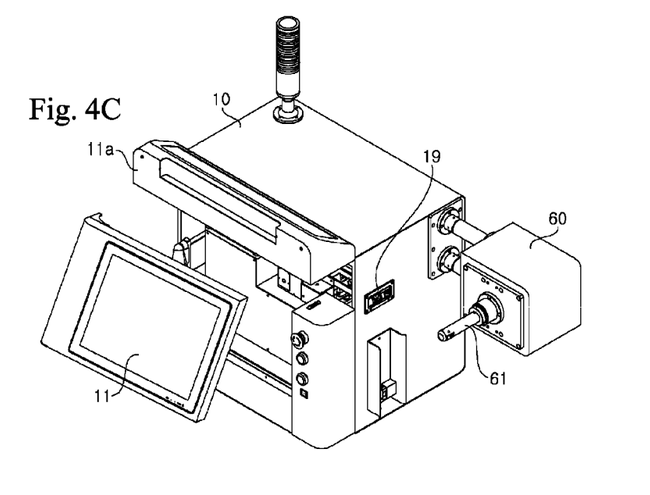

Meanwhile, as shown in FIGS. 4A to 4C, with the medicine package inspection apparatus according to the present example embodiment, the displaying means 11 is pivotably and tiltably mounted on the front surface of the body 10 by the pivoting and tilting unit. To this end, the pivoting and tilting unit includes a pivoting member 12 interposed between the body 10 and the displaying means 11. In more detail, one end of the pivoting member 12 is pivotably installed on an inner wall surface of the body 10 through a hinge means 13, and the other end thereof is connected to a rear surface of the displaying means 11.

The displaying means 11 may form a front surface part of the body 10 and open and close an inner portion of the body, together with the cover member 11a. As described above, according to the present invention, the displaying means 11 configures a portion of the body 10, such that an entire size of the medicine package inspection apparatus may be decreased as compared with the case in which the displaying means is separately mounted outside the body 10.

A first connection member 14 is connected to the other end of the pivoting member 12 through a first rotation axis 14a in a vertical direction and a second connection member 15 is connected to the first connection member 14 through a second rotation axis 15a in a horizontal direction so that the display means 11 may be positioned at an angle desired by the user by changing a connection angle of the displaying means 11 to the other end of the pivoting member 12. The second connection member 15 is fixed to the rear surface of the displaying means 11.

Therefore, the displaying means 11 may be configured so as to pivot around a pivot axis of the hinge means 13 to which one end of the pivoting member 12 is connected to open the inner portion of the body 10, as shown in FIG. 4A, and be configured to pivot around the first rotation axis 14a of the first connection member 14 to allow the user to arbitrarily change a direction toward which the displaying means 11 is directed, as shown in FIG. 4B. In addition, as shown in FIG. 4C, the user may pivot the displaying means 11 around the second rotation axis 15a of the second connection member 15 to allow the displaying means 11 to be obliquely directed upwardly at any angle. Therefore, the user may very easily and conveniently adjust the displaying means 11 so as to be directed toward a direct desired by him/her.

As described above, the pivoting member 12, the hinge means 13, and the first and second connection members 14 and 15 configure the pivoting and tilting unit for pivotably and tiltably mounting the displaying means 11 with respect to the body 10.

The medicine package inspection apparatus according to the present example embodiment may have a volume decreased as compared with the related art to thereby be compact, such that it may be used in a state in which it is put on a table. Here, since the user may freely adjust a direction of the displaying means 11 through the pivoting and tilting unit, the medicine package inspection apparatus may be very conveniently used.

In addition, when the work of inspecting the medicine package is performed in a state in which the cover member 11a pivots upwardly as shown in FIGS. 4A to 4C, since it is easy to access a path through which the medicine package is conveyed, the user may rapidly take action when the medicine package is not smoothly conveyed or a new medicine package bundle is supplied, which is advantageous.

Hereinafter, a medicine package inspection apparatus according to a second example embodiment of the present invention will be described with reference to FIGS. 5 to 6C.

Figure 5:
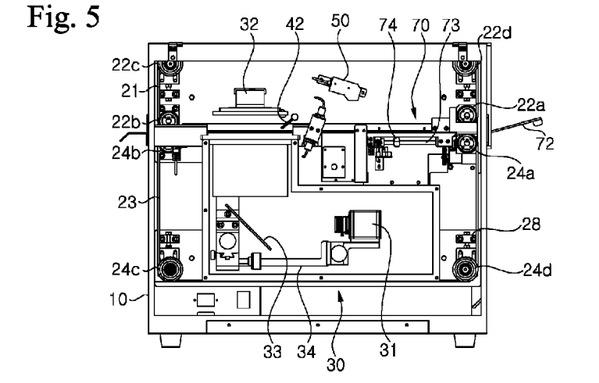
FIG. 5 is a front cross-sectional view showing a medicine package inspection apparatus according to a second example embodiment of the present invention.

As shown in FIG. 5, the medicine package inspection apparatus according to a second example embodiment of the present invention includes a conveying unit 20 (See FIG. 3) installed in a body 10 and conveying a medicine package bundle in which a plurality of medicine packages are continuously connected to each other to one side (from the right to the left when viewed in FIG. 2), an image reading unit 30 photographing the medicine packages conveyed by the conveying unit 20 and reading the number and states of the medicines by the photographed image, and an aligning unit 70 uniformly spreading the medicines packaged in the medicine packages of the medicine package bundle conveyed to the image reading unit 30 so as not to be overlapped with each other, similar to the medicine package inspection apparatus according to a first example embodiment of the present invention described above.

In addition, the medicine package inspection apparatus according to the second example embodiment of the present invention may further include a recognizing unit 50 that may recognize a mark such as a barcode, or the like, printed on a surface of the medicine package so as to detect information on the number and a kind of medicines that should be packaged in the medicine package that is being inspected, similar to the medicine package inspection apparatus according to the first example embodiment of the present invention described above.

A displaying means 11 that may display a work state simultaneously with controlling a work of inspecting the medicine package is installed on a front surface of the body 10 of the medicine package inspection apparatus according to the second example embodiment of the present invention, and a cover member 11a that may open an inner portion of the body 10 when a user is to directly confirm the work state of the work of inspecting the medicine package with the naked eyes is installed at an upper end of the front surface of the body, as shown in FIG. 1.

Similar to the medicine package inspection apparatus according to the first example embodiment of the present invention described above, in the medicine package inspection apparatus according to the second example embodiment of the present invention, the displaying means 11 may be configured of, for example, a touch screen, or the like, and may be pivotably installed on the body 10 through the pivoting and tilting unit as described above with reference to FIGS. 4A to 4C.

In the following description for the medicine package inspection apparatus according to the second example embodiment of the present invention, components that are the same as those of the medicine package inspection apparatus according to the first example embodiment of the present invention described above will be denoted by the same reference numerals and a detailed description thereof will be omitted, and components that are different from those of the medicine package inspection apparatus according to the first example embodiment of the present invention described above will be described in detail.

Figure 6A:
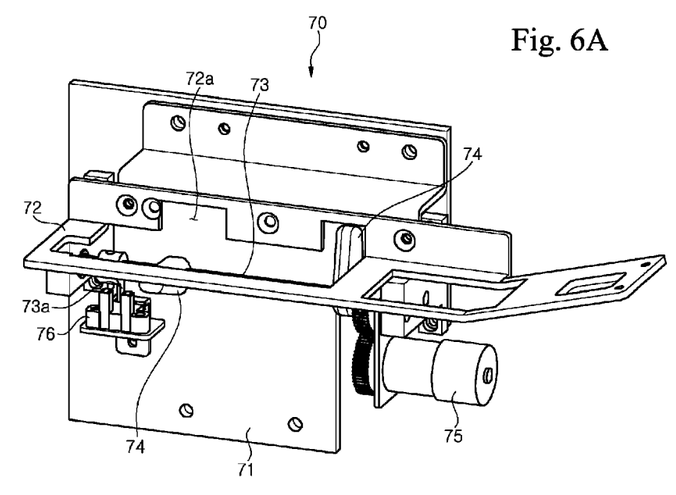
FIGS. 6A to 6C are, respectively, a perspective view, a front view, and a left side view showing a modified example of an aligning unit of the medicine package inspection apparatus according to the second example embodiment of the present invention for uniformly spreading medicines packaged in a medicine package.
Figure 6B:
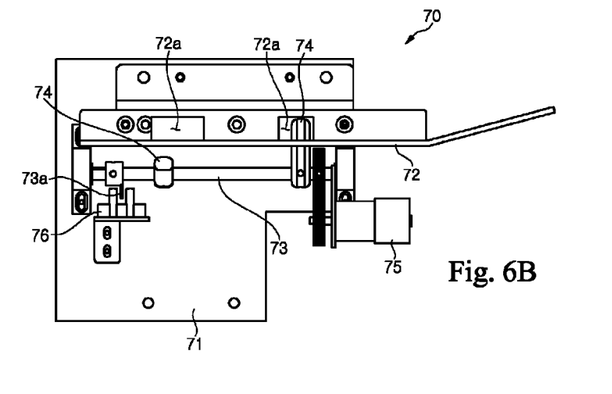
Figures 6C, 7:
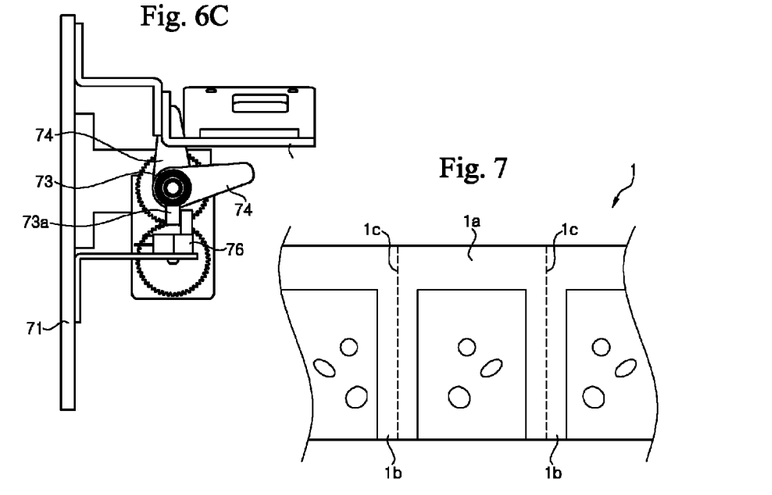
FIG. 7 is a view showing a medicine package supplied to the medicine package inspection apparatus for an inspection.

In FIGS. 6A to 6C, a perspective view, a front view, and a left side view of an aligning unit 70 according to the present example embodiment installed in the medicine package inspection apparatus in order to uniformly spread medicines packaged in a medicine package are shown.

As shown in FIGS. 6A to 6C, the aligning unit 70 according to the second example embodiment of the present invention includes a frame 71 fixed to the body 10 of the medicine package inspection apparatus, a guide plate 72 installed in the frame 71 and guiding moving medicine packages, and a cam member 74, which is an impact means, rotated so as to apply impact to discontinuous fused parts 1b (See FIG. 7) of the medicine packages that are moving along the guide plate 72. The discontinuous fused part 1b of the medicine packages is a part at which a cut line 1c between the medicine packages is formed, that is, a fused part discontinuously formed between the medicine packages in order to partition a medicine accommodating part in one medicine package and a medicine accommodating part in another medicine package from each other.

The number of cam members 74 may be one or more, and in the case in which a plurality of cam members 74 are included in the aligning unit 70, they may be installed on one cam axis 73. The cam axis 73 is installed to receive driving force transferred from a motor 75 through an electric means such as a gear, or the like, to thereby be rotated. It is preferable that in the case in which the plurality of cam members 74 are installed on one cam axis 73, an interval between the cam members 74 is determined depending on a size of the medicine package. That is, the interval between the cam members 74 is determined so as to coincide with or be different from an interval between the discontinuous fused parts 1b formed in the medicine packages by integer times.

The guide plate 72 may include an opening 72a formed therein so as not to hinder rotation of the cam member 74. As described above, the cam member 74 applies impact to the discontinuous fused parts 1b of the medicine package while being rotated. In the case in which the impact is applied to parts in which the medicines are accommodated by the cam member 74, the medicines are not uniformly spread in the medicine package, but may be overlapped with each other, which is not preferable.

Although the case in which two cam members 74 are installed on one cam axis 73 while having a phase difference of approximately 90 degrees therebetween has been shown in FIG. 6C, the number of cam members 74 may also be two or more.

A sensing part 76 is installed in the frame 71 in order to sense a position of the cam member 74, that is, toward which direction the cam member 74 is directed. The sensing part 76 is configured so as to sense a position of a protrusion piece 73a installed on the cam axis 73 to thereby be rotated together with the cam axis 73. In addition, the sensing part 76 may be changed into various forms as long as it may sense a rotation angle of the cam axis 73 on which the cam members 74 are installed.

In the case in which two or more cam members 74 are installed on one cam axis 73, a phase difference between one cam member 74 and another cam member 74 may be arbitrarily determined. However, at least one place at which the phase difference between one cam member 74 and another cam member 74 is 90 degrees or more should be present.

The reason why the phase difference between the cam members 74 should be 90 degrees or more at at least one place is to prevent movement of the medicine package entering along the guide plate 72 at the time of initial entrance from being hindered. According to the present example embodiment, when the entrance of the medicine package is sensed by a sensor (not shown) installed at an upper portion of the aligning unit 70, the controlling part included in the medicine package inspection apparatus drives the motor 75 of the aligning unit 70 to rotate the cam axis 73, thereby orienting the cam members 74 at an angle at which the cam members 74 do not hinder the movement of the medicine packages, and then stops an operation of the motor 75. After the medicine package enters, the controlling part continuously drives the motor 75 to allow the cam members 74 to apply impact to the fused part 1a of the medicine package, thereby aligning the medicines in the medicine package.

As described above, with the medicine package inspection apparatus according to an example embodiment of the present invention, the medicine package is conveyed in a state in which it is fitted between the upper belt 21 and the lower belt 23, such that it may be securely conveyed.

With the medicine package inspection apparatus according to an example embodiment of the present invention, since the camera 31 is installed so as to photograph the medicine package 1 through the reflecting plate 33 without positioning the camera 31 of the image reading unit 30 and the medicine package 1 on the straight line, an increase in an entire size of the medicine package inspection apparatus may be prevented, and an internal space of the medicine package inspection apparatus may be efficiently used. In addition, the bobbin supporting unit 60 that may support the bobbin around which the medicine package bundle having a large volume is wound is installed outside the body 10, thereby making it possible to further decrease the entire size of the medicine package inspection apparatus.

As set forth above, according to example embodiments of the present invention, the medicine package inspection apparatus having a decreased entire size and conveying the medicine packages by the pair of conveyor belts may be provided.

Therefore, with the medicine package inspection apparatus according to example embodiments of the present invention, the medicine packages may be smoothly and securely conveyed at the time of performing an inspection work. In addition, a volume of the medicine package inspection apparatus may be decreased, and the user may easily control an inspection process and easily perform the inspection work.

Hereinabove, although the medicine package inspection apparatus according to example embodiments of the present invention have been described with reference to the accompanying drawing, the present invention is not limited to the example embodiments described above and the accompanying drawings, but may be variously modified and altered by those skilled in the art to which the present invention pertains without departing from the spirit and scope as defined in the claims.

Moreover, aspects and features of the various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A medicine package inspection apparatus for inspecting medicines packaged in medicine packages, wherein the medicine package inspection apparatus confirms whether or not accurate medicines have been packaged, comprising:
   a conveying unit installed in a body for conveying the medicine packages to one side;
   an image reading unit for photographing the medicine packages conveyed by the conveying unit and for reading states of the medicines by the photographed image;
   an aligning unit for uniformly spreading the medicines packaged in the medicine packages conveyed to the image reading unit so that the medicines are not overlapped with each other; and
   a displaying means pivotably installed on a front surface of the body for displaying a work state simultaneously with controlling a work of inspecting the medicine packages,
   wherein the displaying means is pivotably and tiltably installed on the body through a pivoting and tilting unit, and
   wherein the displaying means is configured relative to the body such that an inner portion of the body is opened when an end of the displaying means pivots away from the body.

2. The medicine package inspection apparatus of claim 1, wherein the pivoting and tilting unit includes:
   a pivoting member interposed between the body and the displaying means,
   a hinge means for pivotably connecting one end of the pivoting member to the body,
   a first connection member connected to the other end of the pivoting member so as to be pivotable around an axis line in a vertical direction, and
   a second connection member connected to the first connection member so as to be pivotable around an axis line in a horizontal direction and fixed to the displaying means.

3. The medicine package inspection apparatus of claim 1, wherein the image reading unit includes a camera for photographing a medicine package to be inspected, and a light source for photographing, and
   wherein the photographing is performed through a reflecting plate.

4. The medicine package inspection apparatus of claim 1, wherein the aligning unit includes at least one of:
   a vibration means for vibrating the medicine package by vibrations, and
   a pressing means for applying pressure to the medicine package.

5. The medicine package inspection apparatus of claim 1, further comprising a bobbin supporting unit installed outside the body so as to support a medicine package bundle wound around a bobbin for an inspection, wherein the bobbin supporting unit includes a bobbin mounting axis into which the bobbin is detachably fitted.

6. The medicine package inspection apparatus of claim 1, further comprising:
   a cover member for closing the front surface of the body together with the displaying means, and
   said cover member is moved separately from the displaying means to open an upper end portion of the front surface of the body.

7. The medicine package inspection apparatus of claim 1, wherein the image reading unit photographs the states of the medicines to determine whether a medicine package is an abnormal medicine package, and
   wherein, when the medicine package inspected by the image reading unit is determined to be an abnormal medicine package, the conveying unit reverses a conveying direction of the medicine package so that the abnormal medicine package is returned to the aligning unit.

8. The medicine package inspection apparatus of claim 7, wherein the abnormal medicine package is a medicine package in which a plurality of medicines are at least partially overlapped with each other, or a medicine package in which a plurality of medicines contact each other to thereby be recognized as if they are one medicine.

9. The medicine package inspection apparatus of claim 1, wherein:
   the conveying unit includes an upper conveyor apparatus having an upper belt and a plurality of upper rollers,
   the conveying unit includes a lower conveyor apparatus having a lower belt and a plurality of lower rollers, and
   the medicine packages are conveyed in a state in which they are fitted between the upper belt and the lower belt.

10. The medicine package inspection apparatus of claim 9, wherein the upper conveyor apparatus and the lower conveyor apparatus receive driving power transferred from one driving source to thereby be driven.

11. The medicine package inspection apparatus of claim 9, wherein the upper conveyor apparatus and the lower conveyor apparatus include a tension adjusting means for adjusting tension degrees of the upper belt and the lower belt, respectively.

12. The medicine package inspection apparatus of claim 1, wherein the aligning unit includes an impact means for applying an impact to discontinuous fused parts, and
   wherein said discontinuous fused parts are discontinuously formed between the medicine packages in order to partition a medicine accommodating part in one medicine package and a medicine accommodating part in another medicine package from each other.

13. The medicine package inspection apparatus of claim 12, wherein the aligning unit includes a guide plate guiding movement of the medicine package, and
   the impact means is a cam member for applying an impact to the medicine packages that are being moved along the guide plate, and wherein the cam member is installed on a cam axis and is rotated by a motor in order to be rotated together with the cam axis.

14. The medicine package inspection apparatus of claim 13, wherein a plurality of cam members are installed on a common cam axis to rotate together about the common cam axis, and
at least one of the plurality of cam members forms an angle of 90 degrees or more with respect to the other cam member.

15. The medicine package inspection apparatus of claim 13, wherein the aligning unit includes a protrusion piece installed on the cam axis, and a sensing part for sensing a position of the protrusion piece to detect a position of the cam member.

* * * * *